(12) United States Patent
Yang et al.

(10) Patent No.: US 6,934,035 B2
(45) Date of Patent: Aug. 23, 2005

(54) SYSTEM AND METHOD FOR MEASURING OPTICAL DISTANCE

(75) Inventors: Changhuei Yang, Singapore (SG); Adam Wax, Boston, MA (US); Ramachandra R. Dasari, Lexington, MA (US); Michael S. Feld, Newton, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 341 days.

(21) Appl. No.: 10/024,455

(22) Filed: Dec. 18, 2001

(65) Prior Publication Data

US 2003/0112444 A1 Jun. 19, 2003

(51) Int. Cl.[7] .................................................. G01B 9/02
(52) U.S. Cl. ........................ 356/485; 356/486; 356/497
(58) Field of Search ................................ 356/485, 486, 356/489, 497, 479, 496, 484

(56) References Cited

U.S. PATENT DOCUMENTS 3,970,389 A * 7/1976 Mendrin et al. .............. 356/4.1
4,492,464 A * 1/1985 Bourdet et al. .............. 356/4.1

(Continued)

FOREIGN PATENT DOCUMENTS

| DE | 3328773 A | 3/1984 |
| EP | 0 932 050 A2 | 7/1999 |
| JP | 9061109 A | 3/1997 |
| RU | 2020409 C | 9/1994 |
| SU | 1357712 A | 12/1987 |
| WO | WO 89/06781 | 7/1989 |
| WO | WO 01/01849 A1 | 1/2001 |

OTHER PUBLICATIONS

Xiaoli D., et al., "High–Accuracy Absolute Distance Measurement by Means of Wavelength Scanning Heterodyne Interferometry," Measurement Science and Technology, IOP Publishing, Bristol, GB, vol. 9, No. 7, Jul. 1998, p. 1031–1035.

Primary Examiner—Gregory J. Toatley, Jr.
Assistant Examiner—Patrick Connolly
(74) Attorney, Agent, or Firm—Weingarten, Schurgin, Gagnebin & Lebovici LLP

(57) ABSTRACT

The methods of the present invention are directed at an accurate phase-based technique for measuring arbitrarily long optical distances with sub-nanometer precision. A preferred embodiment of the present invention method employs a interferometer, for example, a Michelson interferometer, with a pair of harmonically related light sources, one continuous wave (CW) and a second source having low coherence. By slightly adjusting the center wavelength of the low coherence source between scans of the target sample, the phase relationship between the heterodyne signals of the CW and low coherence light is used to measure the separation between reflecting interfaces with sub-nanometer precision. As the preferred embodiment of this method is completely free of $2\pi$ ambiguity, an issue that plagues most phase-based techniques, it can be used to measure arbitrarily long optical distances without loss of precision.

38 Claims, 11 Drawing Sheets

U.S. PATENT DOCUMENTS

| | | | |
|---|---|---|---|
| 4,702,603 A | 10/1987 | Augustyn | 356/351 |
| 4,938,584 A | 7/1990 | Suematsu et al. | 351/211 |
| 5,018,862 A | 5/1991 | Aiello | 356/358 |
| 5,153,669 A | 10/1992 | DeGroot | 356/349 |
| 5,263,776 A | 11/1993 | Abraham et al. | 374/161 |
| 5,349,440 A | 9/1994 | DeGroot | 356/349 |
| 5,371,587 A | 12/1994 | de Groot et al. | 356/349 |
| 5,404,221 A * | 4/1995 | de Groot | 356/486 |
| 5,412,474 A | 5/1995 | Reasenberg et al. | 356/349 |
| 5,459,570 A * | 10/1995 | Swanson et al. | 356/479 |
| 5,543,914 A | 8/1996 | Henshaw et al. | 356/345 |
| 5,579,109 A | 11/1996 | Suh et al. | 356/349 |
| 5,589,641 A | 12/1996 | Johnson et al. | 73/800 |
| 5,706,084 A | 1/1998 | Gutierrez | 356/351 |
| 5,737,069 A * | 4/1998 | Nashiki et al. | 356/5.13 |
| 5,781,295 A | 7/1998 | Fuchs et al. | 356/349 |
| 6,015,969 A * | 1/2000 | Nathel et al. | 250/227.27 |
| 6,359,692 B1 * | 3/2002 | Groot | 356/512 |
| 6,495,833 B1 * | 12/2002 | Alfano et al. | 250/341.8 |
| 6,611,339 B1 * | 8/2003 | Yang et al. | 356/485 |
| 6,657,727 B1 * | 12/2003 | Izatt et al. | 356/450 |
| 6,847,456 B2 * | 1/2005 | Yang et al. | 356/489 |

* cited by examiner

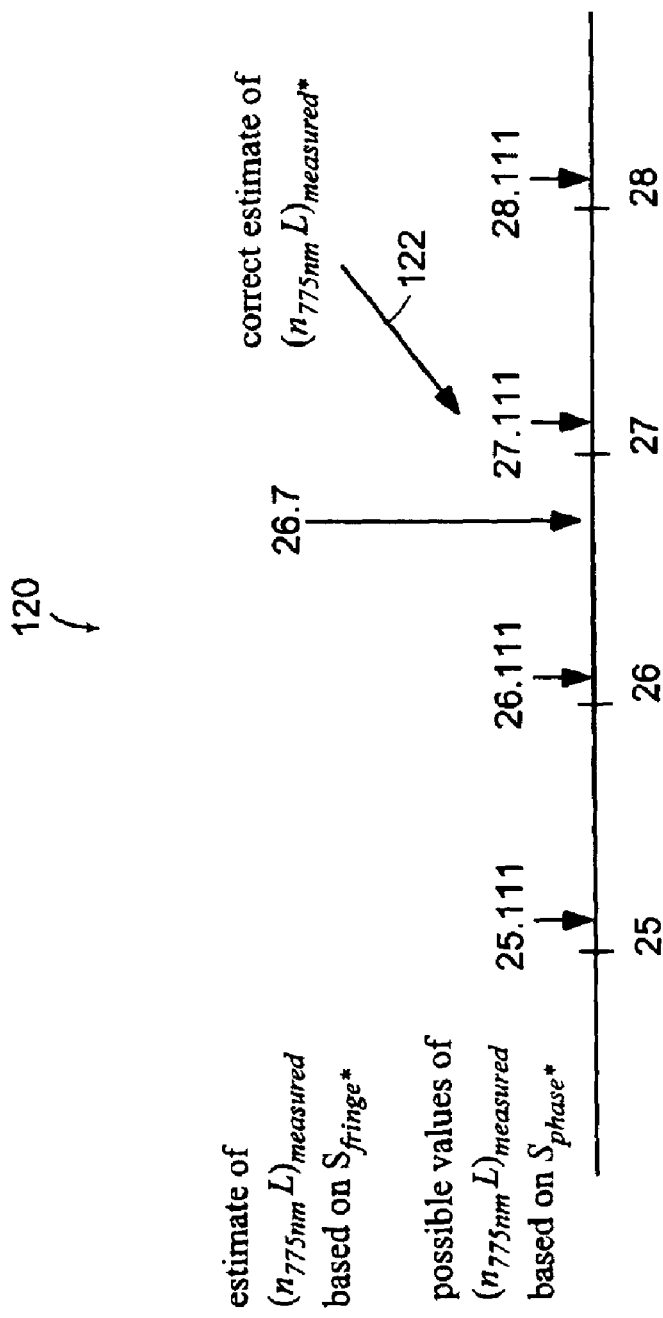

SYSTEM AND METHOD FOR MEASURING OPTICAL DISTANCE

GOVERNMENT SUPPORT

The invention was supported, in whole or in part, by a Grant No. P41-RR02594 from the National Institutes For Health. The Government has certain rights in the invention.

BACKGROUND OF THE INVENTION

Phase-based optical interferometric techniques are widely employed in optical distance measurements in which subwavelength distance sensitivity is required. Optical distance is defined as the product of the refractive index and the length. However, most such techniques are limited by an issue which is widely known in the field as $2\pi$ ambiguity or integer ambiguity which can be defined as the difficulty in telling the interference fringes of an axial scan apart from each other. An unmodified harmonic phase based low coherence interferometry method (HPI) can be used to determine the differential optical distance, $(n_{\lambda_2} - n_{\lambda_1})L$, where L is the physical distance, $n_{\lambda_1}$ and $n_{\lambda_2}$ are the refractive indices at the wavelengths $\lambda_1$ and $\lambda_2$ respectively, if the optical distance is increased gradually so that the differential phase measured by HPI can be tracked through its $2\pi$ wrap over. To determine $(n_{\lambda_2} - n_{\lambda_1})$ for DNA in solution, for example, the DNA concentration is gradually increased in the measuring cuvette. While such a measurement approach works well in a controlled environment, it can hardly be implemented in a situation where there is less manipulability in the sample. For example, the method does not work on a fixed slab of material which we are constrained to keep whole.

The problem lies in the fact that unmodified HPI is unable to tell the interference fringes of an axial scan apart from each other, described herein as the $2\pi$ ambiguity issue. It is a problem that plagues most phase-based optical interferometric techniques. As a result, these techniques are unable to determine optical distance absolutely. Therefore, most such techniques are used in applications, such as evaluating the texture of continuous surfaces or detecting time-dependent distance changes, in which phase unwrapping is possible through comparison of phases between adjacent points or over small time increments.

SUMMARY OF THE INVENTION

The methods of the present invention are directed at an accurate phase-based technique for measuring arbitrarily long optical distances, preferably with sub-nanometer precision. A preferred embodiment of the present invention employs an interferometer, for example, a Michelson interferometer, with harmonically related light sources, one continuous wave (CW) and a second source having low coherence (LC). The low coherence source provides a broad spectral bandwidth, preferably a bandwidth of greater than 5 nm for a 1 micron ($\mu$) wavelength, for example, the required bandwidth can vary as a function of wavelength and application. By slightly adjusting the center wavelength of the low coherence source between scans of the target sample, the phase relationship between the heterodyne signals of the CW and low coherence light can be used to measure the separation between reflecting interfaces with sub-nanometer precision. As this technique is completely free of $2\pi$ ambiguity, an issue that plagues most phase-based techniques, it can be used to measure arbitrarily long optical distances without loss of precision. An application of a preferred embodiment of the method of the present invention is the precision determination of the refractive index of a sample at a given wavelength of a sample with a known physical thickness. Another application of a preferred embodiment of the method of the present invention is the precision determination of a sample's physical thickness with a known refractive index. A further application of a preferred embodiment of the method of the present invention is the precision determination of the refractive index ratio at two given wavelengths.

In an alternate preferred embodiment, the low coherence light source provides a sufficiently broad bandwidth light, preferably greater than 5 nm, to provide simultaneously a first low coherence wavelength and a second low coherence wavelength with the respective center wavelengths separated from each other by more than approximately 2 nm. The frequency spectrums for the low coherence wavelengths do not significantly overlap. An additional detector and filters are disposed in the interferometer to transmit and detect the two low coherence wavelengths.

The preferred embodiment methods can be used to make precise optical distance measurements. From such measurements, optical properties of target objects can be accurately measured. By measuring the dispersion profile of the target, structural and/or chemical properties of the target can be evaluated. The dispersion profile maps out the refractive index differences at various wavelengths. In the biomedical context, preferred embodiments of the present invention can be used to accurately determine the dispersion properties of biological tissues in a non-contact and non-invasive manner. Such dispersion determination can be used on the cornea or aqueous humor of the eye. The sensitivity achieved can be sufficient to detect glucose concentration dependent optical changes. In a preferred embodiment of the present invention method, the blood glucose level can be determined through non-invasive measurements of the dispersion profile of either the aqueous, vitreous and/or aqueous and/or aqueous humor or the cornea of the eye. A preferred embodiment of the present invention can be applied as a measurement technique in semiconductor fabrication to measure small features formed during the manufacturing of integrated circuits and/or optoelectronic components. As the preferred embodiment of the method is non-contact and non-destructive, it can be used to monitor the thickness of semiconductor structures or optical components as they are being fabricated.

BRIEF DESCRIPTION OF THE DRAWINGS

FIG. 5 illustrates a method of determining correct estimates of ($n_{755nm}$L) measured by choosing the values that minimizes the error between estimates based on $S_{phase}$ and $S_{fringe}$ in accordance with a preferred embodiment of the present invention;

Figure 1:
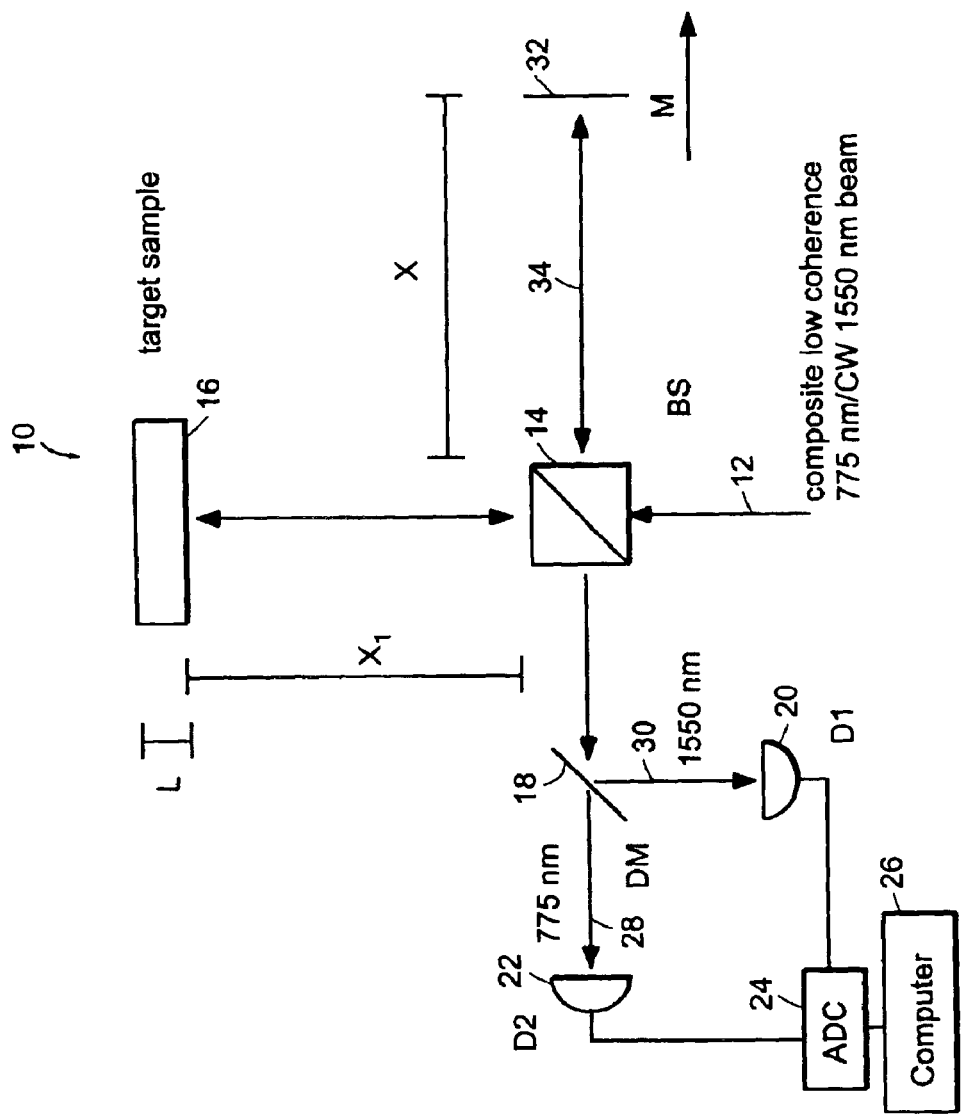
FIG. 1 is a schematic diagram of a preferred embodiment of the system to measure an optical distance in accordance with the present invention.

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

DETAILED DESCRIPTION OF THE INVENTION

The present invention is directed at phase crossing based systems and methods for measuring optical distances that overcome the integer or 2π ambiguity problem by introducing a dispersion imbalance in an interferometer. A preferred embodiment of the method is able to measure the relative height difference of two adjacent points on a surface with precision. Further, the refractive index of a sample can be found to an accuracy that is limited only by the precision with which the physical thickness of the sample can be experimentally measured.

The substitution of one of the low coherence light sources with a continuous wave (CW) light source in the harmonic phase based interferometry (HPI), allows the use of the associated CW heterodyne signal as a form of optical ruler by which the low coherence heterodyne signal can be measured. The low coherence light source provides a spectral bandwidth, for example, greater than 5 nm for 1 micron wavelength. One of the benefits of using such a modified HPI is that the measured phase is now sensitive to the length scale nL instead of $(n_{\lambda_2}-n_{\lambda_1})$L, where n is the refractive index at the low coherence wavelength. The quantity n is more practically useful than the composite $(n_{\lambda_2}-n_{\lambda_1})$. By adjusting the low coherence wavelength slightly, for example, by approximately 2 nm, the quantity nL can be found without 2π ambiguity and with sub-nanometer sensitivity. This method uses the CW heterodyne interference signal as a reference optical ruler by which the optical distance is measured.

Interferometric optical distance measuring systems employing readily available low coherence light sources have achieved resolution on the order of tens of wavelengths. While this technique is relatively insensitive, it does not have to contend with the 2π ambiguity issue. A preferred embodiment includes a low coherence interferometry method that uses phase to measure arbitrarily long optical distances with sub-nanometer precision. This method uses a low coherence phase crossing technique to determine the integer number of interference fringes, and additional phase information from the measurement to accurately obtain the fractional fringe. In addition, it provides depth resolution and can be used for tomographic profiling of stratified samples. As the method can measure long optical distances with precision, it can be used to determine refractive indices of a plurality of materials accurately. As this is a phase-based method, the refractive index thus found is the phase refractive index and not the group refractive index.

FIG. 1 illustrates a preferred embodiment of the system 10 of the present invention that includes a modified Michelson interferometer. The input light 12 is a two-color composite beam composed of 150-fs mode-locked light from a Ti:sapphire laser, for example, emitting at 775.0 nm and continuous wave (CW) 1550.0 nm light from, for example, a semiconductor laser. In the preferred embodiment the method evaluates optical distances in terms of the CW wavelength, (1550.0 nm exactly in this embodiment) and all optical distances are computed based on this basis. The composite beam is divided in two at the beamsplitter 14. One part signal is incident on the target sample 16, while the other is incident on a reference mirror 32 moving preferably at, for example, approximately 0.5 mm/s, which induces a Doppler shift on the reference beam 34. The Doppler shift can be induced by other means, such as, for example, through the use of an electro-optical modulator. The back-reflected beams are recombined at the beamsplitter 14, separated into their wavelength components by means of a dichroic mirror 18, and measured separately with photodetectors 20, 22. The resulting signals are digitized by an analog to digital converter (ADC) 24 such as, for example, a 16-bit 100 KHz A/D converter. A data processor such as a personal computer (PC) 26 is in communication with the ADC 24 to further process the data. The resulting heterodyne signals at their respective Doppler-shifted frequencies are bandpassed around their respective center heterodyne frequencies and Hilbert transformed to extract the corresponding phases of the heterodyne signals, $\Psi_{CW}$ and $\Psi_{LC}$. The subscripts CW and LC denote the 1550.0 nm continuous wave and 775.0 nm low coherence wavelength components, respectively.

The center wavelength of low coherence light is then adjusted by approximately 1–2 nm and a second set of $\Psi_{CW}$ and $\Psi_{LC}$ values is measured. From these two sets of readings, the various interfaces in the target sample can be localized with sub-nanometer precision. The processing of data for localization is described hereinbelow.

Consider a sample which consists of a single interface at an unknown distance $x_1$ from the beamsplitter 14. The distance from the beamsplitter 14 to the reference mirror 32, x, is a known quantity at each time point in the scan of the reference mirror.

A method to find an approximate value for $x_1$ is by scanning x and monitoring the resulting heterodyne signal in the recombined low coherence light beam. When x is approximately equal to $x_1$, a peak in the heterodyne signal amplitude is expected. The precision of such a method is limited by the coherence length, $l_c$, of the light source and the signal-to-noise quality of the heterodyne signal. Under realistic experimental conditions, the error in $x_1$ determined thus, is unlikely to be better than a fifth of the coherence length.

Given that the coherence length of a typical low coherence source is approximately 10 µm nominally, this means that the error in such a means of length determination is limited to about 2 µm.

In considering the phase of the heterodyne signal, the varying component of the heterodyne signal detected can be expressed as:

$$I_{heterodyne} = E_{ref}e^{i(2kx-\omega t)}E_{sig}e^{-i(2kx_1-\omega t)} + c.c., \quad (1)$$
$$= 2E_{ref}E_{sig}\cos(2k(x-x_1))$$

where $E_{ref}$ and $E_{sig}$ are the electric field amplitude of the reference and signal electric field amplitude, respectively, k is the optical wavenumber, ω is the optical frequency. The factor of 2 in the exponents is due to the fact that light travels twice the path going to the mirror/sample and back to the beamsplitter.

Note that when x matches $x_1$ exactly, the heterodyne signal is expected to peak. The two returning beams are in constructive interference. This property is therefore used to localize the interface. $x_1$ is found by finding the value of x for which the two beams are in constructive interference. Since phase can be measured accurately, such an approach gives a length sensitivity of about 5 nm. Unfortunately, this method is calculation intensive because there are multiple values of x for which the heterodyne signal peaks; specifically, the heterodyne signal peaks at:

$$x = x_1 + a\frac{\lambda}{2}, \quad (2)$$

where a is an integer and λ is the optical wavelength. This is a manifestation of the 2π ambiguity issue.

Figure 2:
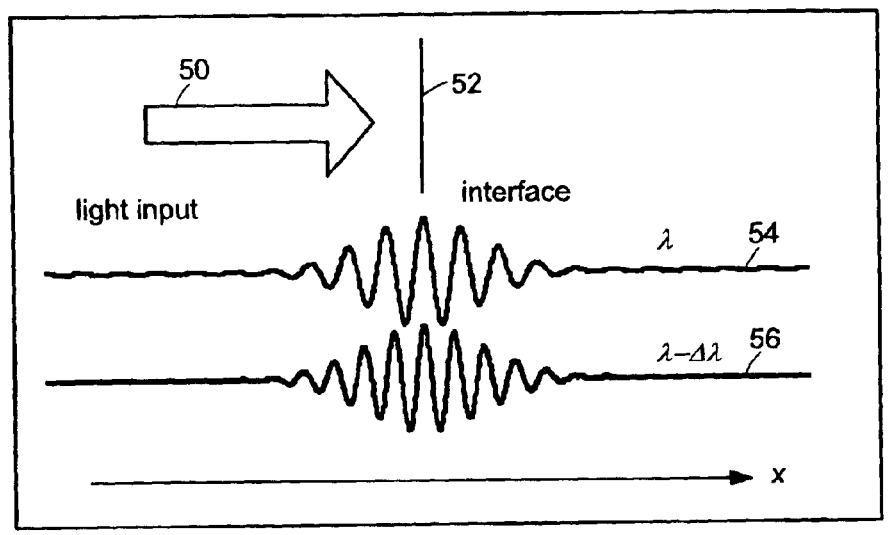
FIG. 2 illustrates the low coherence heterodyne signals associated with a reflecting interface in accordance with a preferred embodiment wherein adjusting the low coherence wavelength compresses or expands (depending on the direction of adjustment of the center wavelength of the low coherence source) the heterodyne signal around the interface.

The preferred embodiment includes a method to distinguish the correct peak. Note that when x=$x_1$ exactly, the heterodyne signal peaks regardless of the optical wavelength. On the other hand, the subsequent peaks are wavelength dependent, as illustrated in FIG. 2. FIG. 2 illustrates the low coherence heterodyne signals associated with the reflecting interface 52 in the sample. Therefore, by adjusting the low coherence wavelength, the heterodyne signal is compressed around the interface and the correct peak associated with the situation where x=$x_1$ exactly can be distinguished. It should be noted that the heterodyne signal may be compressed or expanded around the interface depending upon the direction of adjustment. An intuitive way of visualizing the localization is to picture the heterodyne signal squeezing in or expanding away from the fringe where x=$x_1$ exactly.

Figure 3:
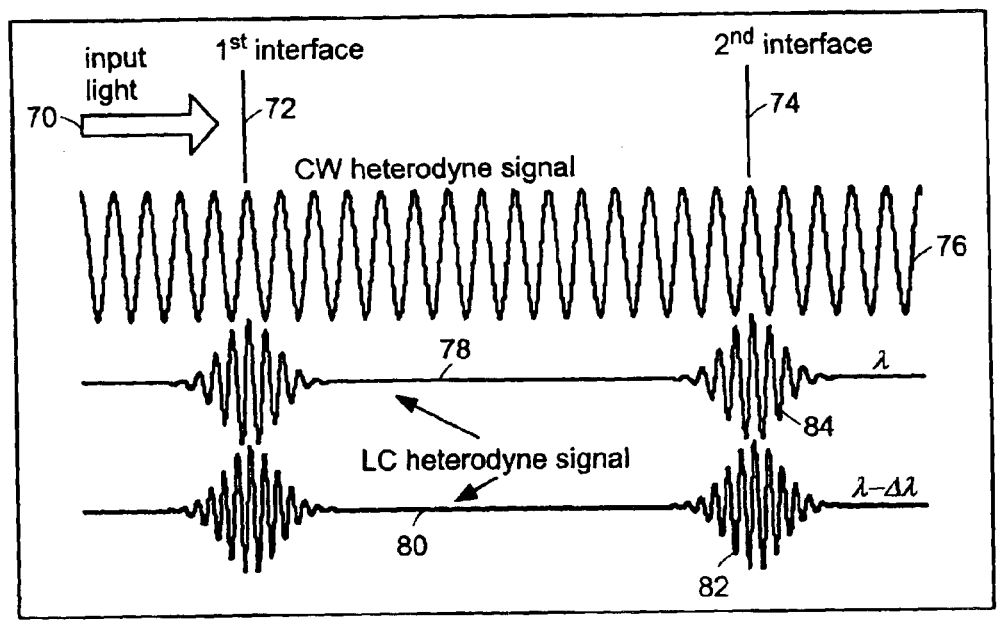
FIG. 3 illustrates heterodyne signals associated with two reflecting interfaces in a sample in accordance with a preferred embodiment wherein decreasing the low coherence wavelength compresses the heterodyne signal around the interfaces.

The CW light source is needed in such a localization method for two reasons. First, it is very difficult in practice to know the value absolutely and accurately in an interferometer. The CW component of the interferometer permits highly accurate measurements of x to be made as the reference mirror is scanned. In a specific preferred embodiment, to determine the distance between two interfaces in the sample, a count of the number of CW interference fringes that occurred between where $x_1$ is equal to the distance to the first interface as shown in FIG. 1 and where $x_2(x_2=x_1+nL$ wherein n is the refractive index of the sample) is equal to the distance to the second interface is made. FIG. 3 illustrates the heterodyne signals associated with two reflecting interfaces in a sample. Adjusting the low coherence wavelength compresses 82, 84 the heterodyne signal 78, 80 around the interfaces.

Second, the prior described method for localization of the interface may partly fail if there is a phase shift associated with the reflection process. For example, if the surface is metallic, the phase shift is non-trivial and the phase of the heterodyne signal takes on some other value when x=$x_1$ exactly. While the prior method allows the correct interference fringe to be identified where x=$x_1$, however sub-wavelength sensitivity may be compromised. The presence of the CW heterodyne signal allows the difference phase via the HPI method to be found. The knowledge of this value, allows the localization of the interface with a high level of sensitivity.

The principle of the HPI method can be illustrated through the exemplary embodiment of a sample of thickness, L, and refractive index, $n_{775nm}$, at a wavelength of 775 nm. The two interfaces of the sample are at optical distances $x_1$ and $x_2$ (where $x_2=x_1+n_{775nm}L$) from the beamsplitter, respectively. Note that the method only works if the optical distance separation is greater than the coherence length, for example, typically between 1 micron and a 100 microns of the low coherence light source. Otherwise, the heterodyne phase signals associated with the interfaces merge together and result in inaccurate interface localization. For clarity of explanation, the incorporation of the phase shifts associated with reflection are deferred until later.

Figure 4:
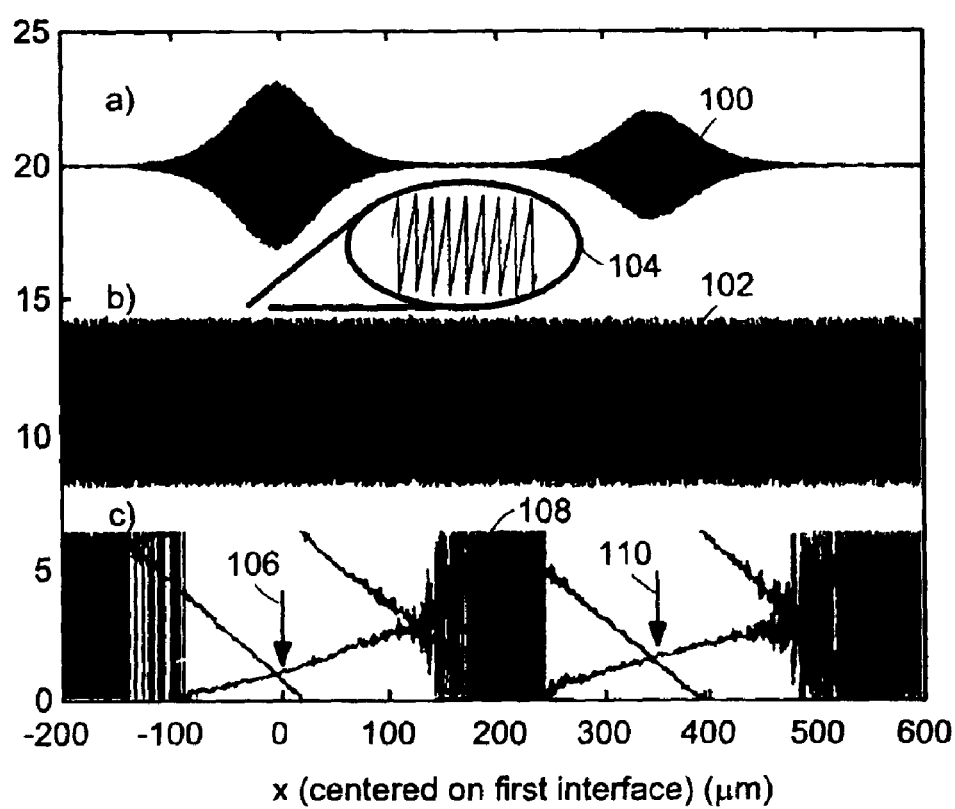
FIG. 4 illustrates a scan of a sample with two interfaces in accordance with a preferred embodiment of the present invention (a) low coherence heterodyne signal, (b) trace wherein the magnified view shows the phase fringes, each fringe corresponds to an optical distance of $\lambda_{CW}$, (c) traces at two difference values of Δ, wherein the arrows indicate the phase crossing points, the vertical axis is in radians.

FIG. 4 is a scan illustrating the mathematical description. The scan is of a sample with two interfaces. The signal 100 is a low coherence heterodyne signal. The trace 102 is $\psi_{CW}(x)$. The magnified view 104 shows the phase fringes. Each fringe corresponds to an optical distance of $\lambda_{CW}$. The lower traces of $\psi_D(x)$ are at two different values of Δ. The arrows 106, 110 indicate the phase crossing points. The vertical axis is in radians. As the reference mirror is scanned, the phase of the low coherence heterodyne signal is given by:

$$\psi_{LC}(x) = \text{mod}_{2\pi}\left(\arg\left(R_{LC,1}e^{i2k_{LC}(x-x_1)}e^{-(2a(x-x_1))^2}\right.\right. +$$
$$\left.\left. R_{LC,2}e^{i2k_{LC}(x-x_2)}e^{-(2a(x-x_2))^2}\right)\right)$$
$$\approx h_c(x-x_1)\text{mod}_{2\pi}(2k_{LC}(x-x_1)) + h_c(x-x_2)\text{mod}_{2\pi}(2k_{LC}(x-x_2)),$$

with $R_{LC\ j}$ the reflectivity of the interface j at the low coherence wavelength, k the optical wavenumber, a=4 ln(2)/$l_c$, $l_c$ the coherence length, x the distance of the reference mirror from the beamsplitter, and $h_c(x)$ a piecewise continuous function with value of 1 for $|x|<2\ l_c$ and 0 otherwise. The factors of 2 in the exponents are due to the effective doubling of optical paths in the back reflection geometry. Equation (3) reflects the fact that phase cannot be measured far beyond the coherence envelopes, due to noise. Although the coherence envelops modeled are gaussian in profile, the same phase treatment is valid for profiles of any slowly varying envelope.

The phase of the CW heterodyne signal is given by:

$$\psi_{cw}(x) = \text{mod}_{2\pi}(\arg(R_{cw,1}e^{i2k_{cw}(x-x_1)} + R_{cw,2}e^{i2k_{cw}(x-(x_1+n_{1550nm}L))})) \quad (4)$$
$$= \text{mod}_{2\pi}(\arg(\bar{R}e^{i2k_{cw}(x-\bar{x})}))$$
$$= \text{mod}_{2\pi}(2k_{cw}(x-\bar{x})),$$

with $R_{CW\ j}$ the reflectivity of the interface j at the CW wavelength, $n_{1550nm}$ the sample's refractive index, $\bar{R}$ and $\bar{x}$ the effective average reflectivity and distance from the beamsplitter, respectively. If the center wavelengths of the two light sources are chosen such that $$k_{LC}=2k_{cw}+\Delta, \quad (5)$$

where $\Delta$ is a small intentionally added shift, then a difference phase, $\psi_D$, of the form is obtained:

$$\psi_D(x) = \psi_{LC}(x) - 2\psi_{cw}(x) \qquad (6)$$

$$= h_c(x-x_1)\mathrm{mod}_{2\pi}(4k_{cw}(\overline{x}-x_1)+2\Delta(x-x_1)) +$$
$$h_c(x-x_2)\mathrm{mod}_{2\pi}(4k_{cw}(\overline{x}-x_2)+2\Delta(x-x_2)).$$

The above quantity provides both the approximate number of fringes in the interval $(x_2-x_1)$ and the fractional fringe, which provides sub-wavelength precision.

As the parameter $\Delta$ is varied by a small amount (corresponding to a wavelength shift of approximately 1–2 nm), the slope of $\psi_D(x)$ pivots around the points where $x=x_1$ and $x=x_2$. In other words, the phase scans at different values of $\Delta$ crosses at those points. The optical distance from $x_1$ to $x_2$ can be found by counting the fringes that $\psi_{cw}(x)$ goes through between the two phase crossing points. Twice the quantity thus found is denoted by $S_{fringe}$, which is not an integer value, and corresponds to the number of fringes at the low coherence wavelength. In the event where multiple phase crossing points occur for a single interface, the point that corresponds to the position of the interface can be found by making multiple scans at additional values of $\Delta$. The position of the interface is the only location where $\psi_D(x)$ will cross for all $\Delta$ values.

The phase shift information is used to further localize the interface separation. Specifically, the difference between the phase shifts at $x=x_1$ and $x=x_2$ is:

$$S_{phase} = \frac{\mathrm{mod}_{2\pi}(\psi_D(x=x_1)-\psi_D(x=x_2))}{2\pi} = \frac{\mathrm{mod}_{2\pi}(4k_{cw}(x_2-x_1))}{2\pi}. \qquad (7)$$

This measures the fractional fringe with great sensitivity.

The absolute optical separation $(x_2-x_1)$ can be determined with precision from $S_{fringe}$ and $S_{phase}$ through the following equation:

$$(x_2-x_1)_{measured} = (n_{775nm}L)_{measured} \qquad (8)$$
$$= \frac{\lambda_{cw}}{4}\left(\left[int(S_{fringe})+U\left(\Delta S-\frac{1}{2}\right)-U\left(-\Delta S-\frac{1}{2}\right)\right]+S_{phase}\right)$$

where $\Delta S = res(S_{fringe}) - S_{phase}$ and $U(\ )$ is a unit step function. Here, int( ) and res( ) denote the integer and fractional parts of the argument respectively. The first term localizes the optical distance to the correct integer number of fringes by minimizing the error between $S_{phase}$ and the fractional part of $S_{fringe}$. The error of an optical separation determination is limited only by the measurement error of $S_{phase}$. In an experiment such error translates to an error in $(n_{775nm}L)_{measured}$ of approximately 0.5 nm. The measurement error of $S_{fringe}$ needs only be smaller than half a fringe so that the correct interference fringe can be established; having satisfied this criterion, it does not enter into the error of $(n_{775nm}L)_{measured}$. The maximum measurable optical distance simply depends on the ability of the system to accurately count fringes between two crossing points and the frequency stability of the light sources.

The above equation is a condensed expression of the method for finding the correct fringe and the fractional fringe. The operation can be illustrated through the following example and FIG. 5 which shows the determination of the correct estimate of $(n_{775nm}L)_{measured}$ by choosing the value that minimizes the error between estimates based on $S_{phase}$ and $S_{fringe}$. Assume that $S_{fringe}$ and $S_{phase}$ are 26.7 and 0.111. From the measurement of $S_{phase}$, the optical distance of the value is:

$$(n_{775nm}L)_{measured} = \frac{\lambda_{cw}}{4}(a+0.111), \qquad (9)$$

where a is an integer. Given the value of $S_{fringe}$, the possible values of $(n_{775nm}L)$measured can be limited to the following 3 values:

$$\frac{\lambda_{cw}}{4}(25.111), \frac{\lambda_{cw}}{4}(26.111)$$

and $$\frac{\lambda_{cw}}{4}(27.111).$$

Given that the value of $$\frac{\lambda_{cw}}{4}(27.111)$$

is closest to $$\frac{\lambda_{cw}}{4}(S_{fringe}),$$

it is the correct estimate of $(n_{775nm}L)_{measured}$.

In preferred embodiments for interferometry experiments based on harmonically related light sources, the appropriately chosen pair of light sources and the method of extracting difference phase allows the minimization and preferably the elimination of the effect of jitter in the interferometer, which would otherwise make high precision optical distance measurement impossible. The elimination of jitter also allows the comparison of scans performed at different times.

To demonstrate the capability of a preferred embodiment of the method, the system is used to probe the optical distance between the top and bottom surface of a fused quartz cover slip having a physical thickness, $L=237\pm3$ $\mu$m. In this embodiment there is a $\pi$ phase shift associated with reflection from the first interface, that marks a positive refractive index transition. Hence, there is a $e^{-i\pi}$ term associated with the factors $R_{LC,1}$ and $R_{cw,1}$ in equations (1) and (2). This results in a correction factor of half on $S_{fringe}$ and $S_{phase}$. FIG. 4 shows the result of typical scans at the LC wavelengths of 773.0 nm and 777.0 nm. The results of four scans are summarized in Table 1 which represents measurements of $(n_{755nm}L)$ on a piece of quartz cover slip. The repeatability of the experimental data indicates that the light source are sufficiently stable in frequency.

TABLE 1

|  | $\frac{\lambda_{cw}}{4} S_{fringe} (\mu m)$ | $\frac{\lambda_{cw}}{4} S_{phase} (\mu m)$ | $(n_{775nm}L)_{measured} (\mu m)$ |
|---|---|---|---|
| Set 1 | 350.86 ± 0.17 | 0.3496 ± 0.0004 | 351.0371 ± 0.0004 |
| Set 2 | 351.08 ± 0.17 | 0.3497 ± 0.0004 | 351.0372 ± 0.0004 |
| Set 3 | 351.15 ± 0.16 | 0.3502 ± 0.0004 | 351.0377 ± 0.0004 |

TABLE 1-continued

| | $\frac{\lambda_{cw}}{4}S_{fringe}(\mu m)$ | $\frac{\lambda_{cw}}{4}S_{phase}(\mu m)$ | $(n_{775nm}L)_{measured}(\mu m)$ |
|---|---|---|---|
| Set 4 | 351.04 ± 0.18 | 0.3498 ± 0.0004 | 351.0373 ± 0.0004 |
| Average | | | 351.0373 ± 0.0004 |

The experimental data yields an optical absolute distance measurement with sub-nanometer precision. The optical distance found is associated with the low coherence light source. The CW heterodyne signal serves as an optical ruler. If L of the quartz cover slip is known precisely, $n_{775nm}$ for quartz at the wavelength 775.0 nm can be found to a very high degree of accuracy from $(n_{775nm}L)_{measured}$.

Alternatively, without knowing the exact value of L, the refractive index ratio at two different wavelengths can be determined by measuring the corresponding optical distances using low coherence light at these wavelengths and CW light at their respective harmonics. Using a range of low coherence wavelengths, the dispersion profile of a material can be determined accurately. The dispersion profile maps out the refractive index differences at various wavelengths. The experimental results in accordance with a preferred embodiment predict that a precision of approximately seven significant figures can be achieved with an approximately 1 mm thick sample.

In another preferred embodiment the light sources of the system are changed to a low coherence superluminescent diode (SLD) emitting at 1550.0 nm and a CW Ti:Sapphire laser emitting at 775.0 nm. By adjusting the operating current through the SLD the center wavelength is changed by about 2 nm; this is adequate to achieve phase crossing. Using this preferred embodiment of the present invention system, the optical distance can be measured at 1550.0 nm. Taking the ratio of the result of this measurement with the previous measurement, the ratio of the refractive indices $n_{775nm}/n_{1550nm}$ for quartz can be determined. It should be noted that the index ratios found are for harmonically related wavelengths due to the sources used in the preferred embodiments. Refraction index ratios for other wavelengths can be measured with other appropriate choices of light sources. For comparison, the corresponding data for glass and acrylic plastic are tabulated in Table 2 as measurements of $n_{775nm}/n_{1550nm}$ for different materials.

TABLE 2

| | $n_{775nm}/n_{1550nm}$ |
|---|---|
| Quartz | 1.002742 ± 0.000003 |
| Glass (German borosilicate) | 1.008755 ± 0.000005 |
| Acrylic plastic | 1.061448 ± 0.000005 |

Note that some of the equations used when the low coherence wavelength is half that of the CW wavelength are slightly different from the equations previously presented herein. For example:

$$\psi_{LC}(x) = \mathrm{mod}_{2\pi}\left(\arg\left(R_{LC,1}e^{i2k_{LC}(x-x_1)}e^{-\left(\frac{2}{l_c}(x-x_1)\right)^2} + R_{LC,2}e^{i2k_{LC}(x-x_2)}e^{-\left(\frac{2}{l_c}(x-x_2)\right)^2}\right)\right) \quad (10)$$

$$\approx h_c(x-x_1)\mathrm{mod}_{2\pi}(2k_{LC}(x-x_1)) + h_c(x-x_2)\mathrm{mod}_{2\pi}(2k_{LC}(x-x_2)),$$

$$\psi_{cw}(x) = \mathrm{mod}_{2\pi}(\arg(R_{cw,1}e^{i2k_{cw}(x-x_1)} + R_{cw,2}e^{i2k_{cw}(x-x_1+n_{1550nm}L)})) \quad (11)$$

$$= \mathrm{mod}_{2\pi}(\arg(\overline{R}e^{i2k_{cw}(x-\overline{x})})) = \mathrm{mod}_{2\pi}(2k_{cw}(x-\overline{x})),$$

$$2k_{LC} = k_{cw} + \Delta, \quad (12)$$

$$\psi_D(x) = 2\psi_{LC}(x) - \psi_{cw}(x) \quad (13)$$
$$= h_c(x-x_1)\mathrm{mod}_{2\pi}(4k_{LC}(\overline{x}-x_1) + 2\Delta(x-x_1)) + h_c(x-x_2)\mathrm{mod}_{2\pi}(4k_{LC}(\overline{x}-x_2) + 2\Delta(x-x_2))$$

$$S_{phase} = \frac{\mathrm{mod}_{2\pi}(\psi_D(x=x_1) - \psi_D(x=x_2))}{2\pi} = \frac{\mathrm{mod}_{2\pi}(4k_{cw}(x_2-x_1))}{2\pi}. \quad (14)$$

$$(x_2-x_1)_{measured} = (n_{775nm}L)_{measured} \quad (15)$$
$$= \frac{\lambda_{LC}}{4}\left(\left[int(S_{fringe}) + U\left(\Delta S - \frac{1}{2}\right) - U\left(-\Delta S - \frac{1}{2}\right)\right] + S_{phase}\right)$$

Preferred embodiments of the methods for overcoming $2\pi$ ambiguity is of significant use in applications such as high precision depth ranging and high precision refractive index determination of thin film solid state materials.

The use of the preferred methods can be illustrated through consideration of a slab of glass. There exist systems that can measure the distance from the systems to the averaged center of the glass slab very accurately. There are also systems that can measure the roughness of the glass surface very accurately. A preferred embodiment of the present invention system measures with nanometer sensitivity the thickness of the glass slab end-face.

Figure 6A:
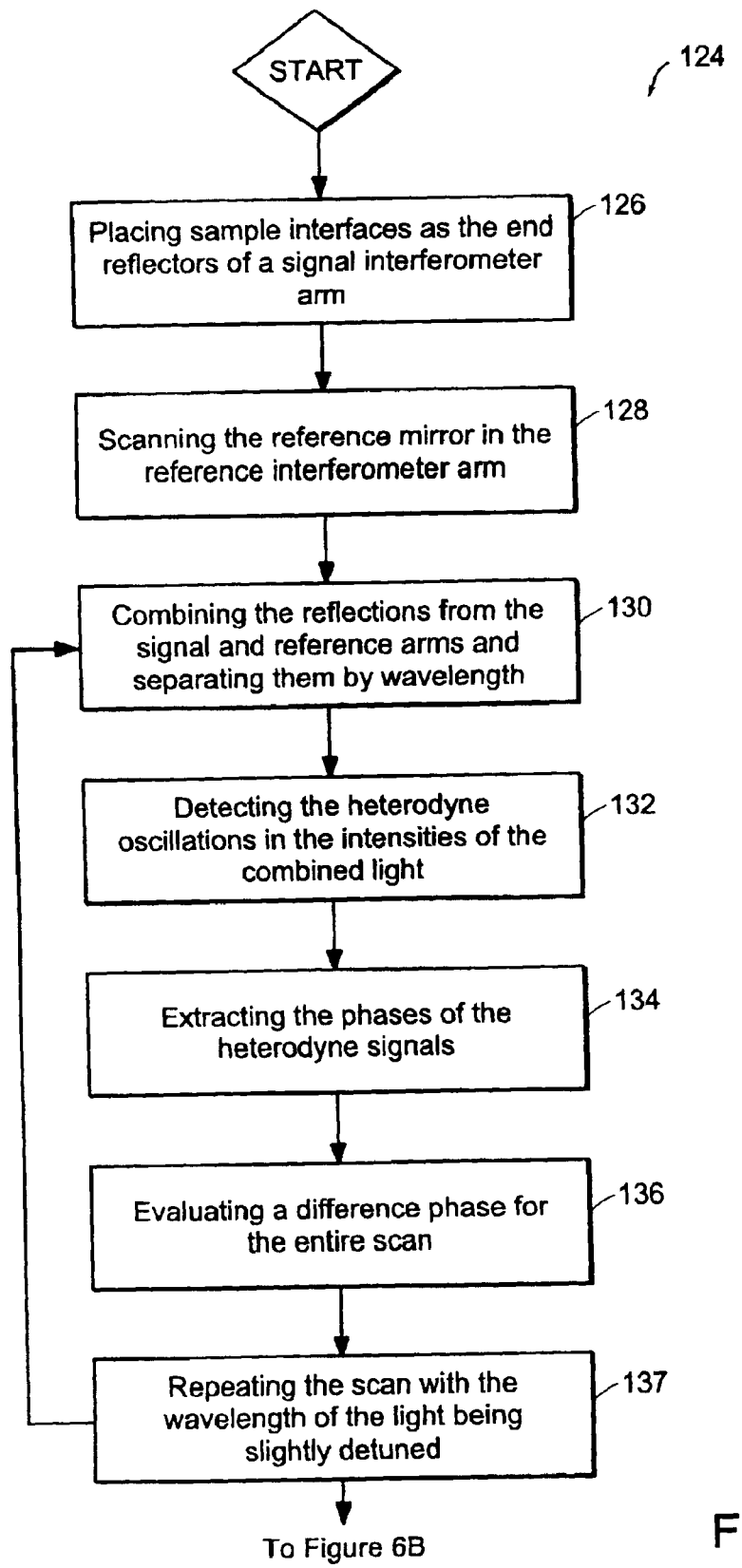
FIGS. 6A and 6B are a flow chart illustrating a method to measure an optical distance in accordance with a preferred embodiment of the present invention.
Figure 6B:
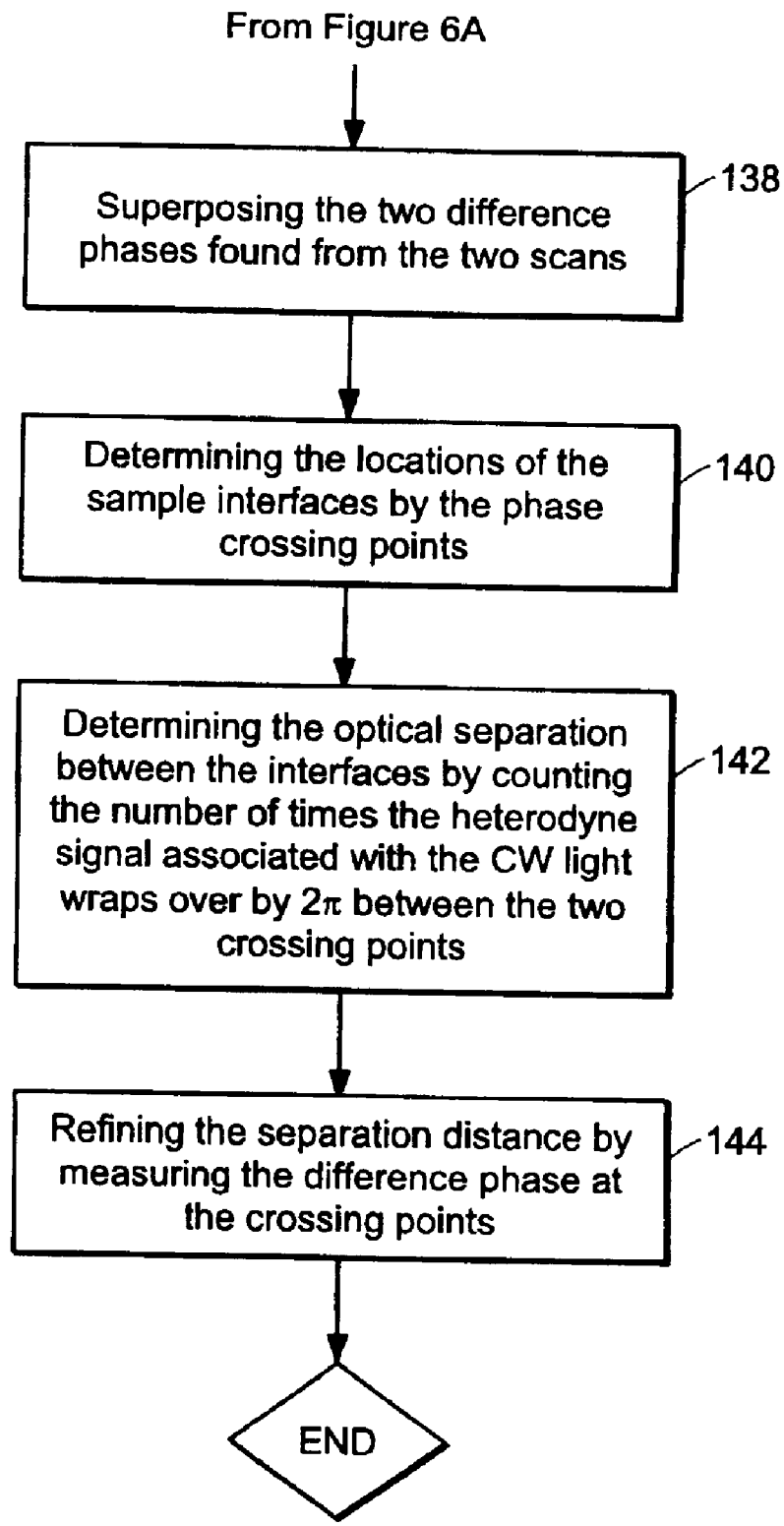

The steps in the implementation of a preferred embodiment of the method to determine the optical distance are illustrated in the flow chart 124 in FIGS. 6A and 6B. The method 124 includes the use of two harmonically related light sources in a Michelson interferometer, one of which is a CW source while the other is a low coherence source. The sample for which the optical distance needs to be measured between its interfaces is used as the end reflectors of the signal interferometer arm per step 126. The reference mirror in the reference interferometer arm is scanned per step 128. The method includes the step 130 in which the reflections from the signal and reference arms are combined and separated by wavelength. Further, per step 132 the heterodyne oscillations in the intensities of the combined light are detected. The phases of the heterodyne signals for both wavelengths are then found via, for example, a Hilbert transform or any alternate phase extraction method per step 134. A difference phase given by subtracting twice the phase of the longer wavelength from the shorter is evaluated for the whole scan per step 136. The scan is repeated with the wavelength of the light being slightly detuned per step 137. Steps 130–136 are then repeated.

The two difference phases found from the two scans are then superposed on each other on a graph with the x-axis representing the displacement of the reference mirror per step 138. It should be noted that the extraction of difference phases can also be done with the appropriate light sources or chromatic filters or software/hardware signal processing on a single scan.

The next step in method 124 includes determining the phase crossing points on a graph to mark the locations of the sample interfaces per step 140. By counting the number of times the heterodyne signal associated with the CW light wraps over by $2\pi$ between the two crossing points, the optical separation between the interfaces is determined per step 142 with accuracy to about a fraction of a wavelength, for example, of approximately 0.2. By measuring the difference phase at the crossing points, further localization and/or refining of the separation to a very small fraction of a wavelength, for example, approximately 0.001.

Figure 7:
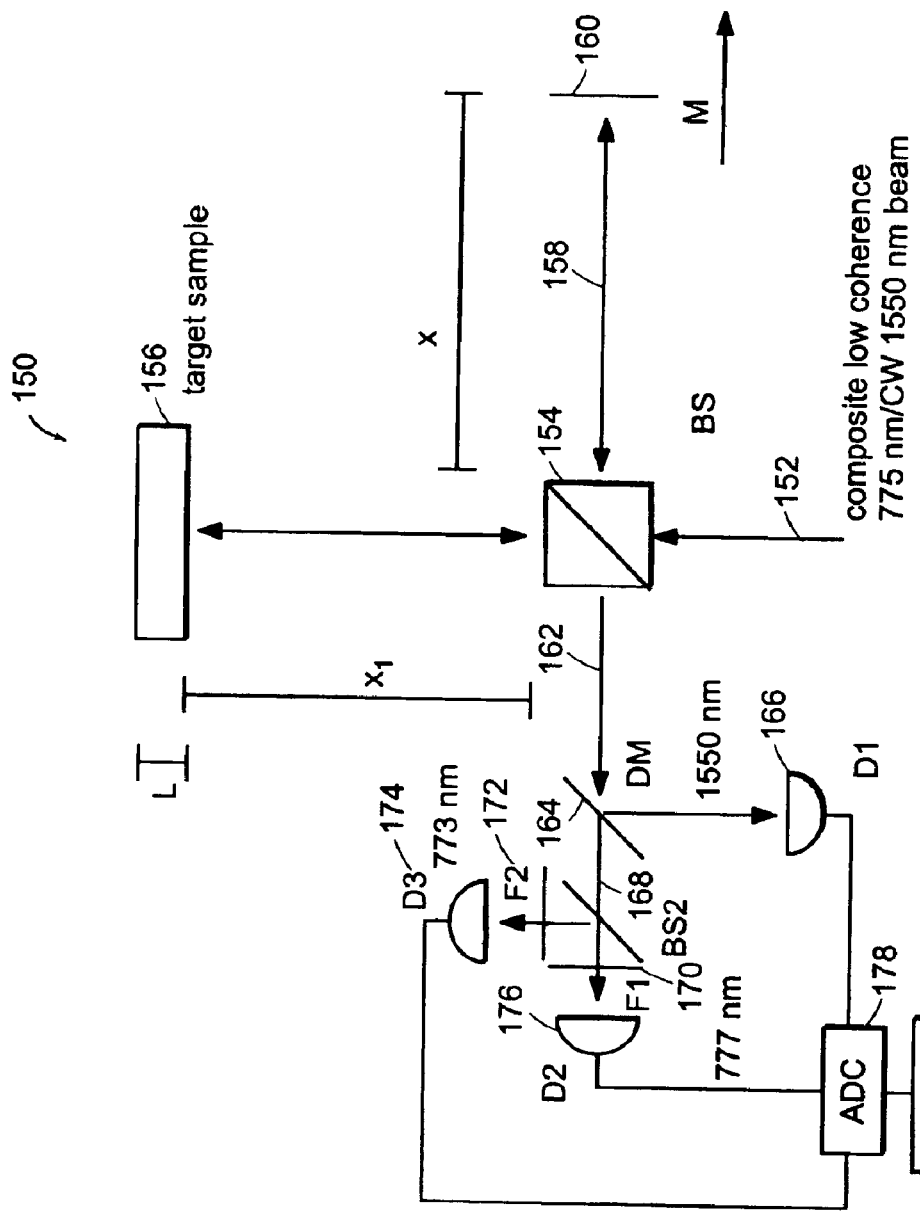
FIG. 7 is a schematic diagram of an alternate preferred embodiment of the system to measure an optical distance in accordance with the present invention.

In another preferred embodiment as illustrated in FIG. 7 which is a schematic diagram of the system to measure optical distance, the low coherence light source may be sufficiently broad in bandwidth, for example, more than 4 nm. On the detection end, a third detector 174 is added to the two detectors 166, 176. This results in the low coherence light signal 168 being further split into two. Prior to reaching the detectors, the two light beams are passed through different filters 170, 172. The filters transmit different parts of the spectrum. One passes the longer wavelength spectra component, while the second, the shorter wavelength spectral component. Preferably the two transmitted beams are separated in their spectrum by more than 2 nm.

The light beams are then incident on the detectors and their heterodyne signals are processed in the fashion discussed with respect to FIG. 1. The advantage of this method in accordance with alternate preferred embodiment is that the method eliminates the repetition of the process with an adjusted low coherence wavelength. The two signals are acquired in the same scan.

Figure 8A:
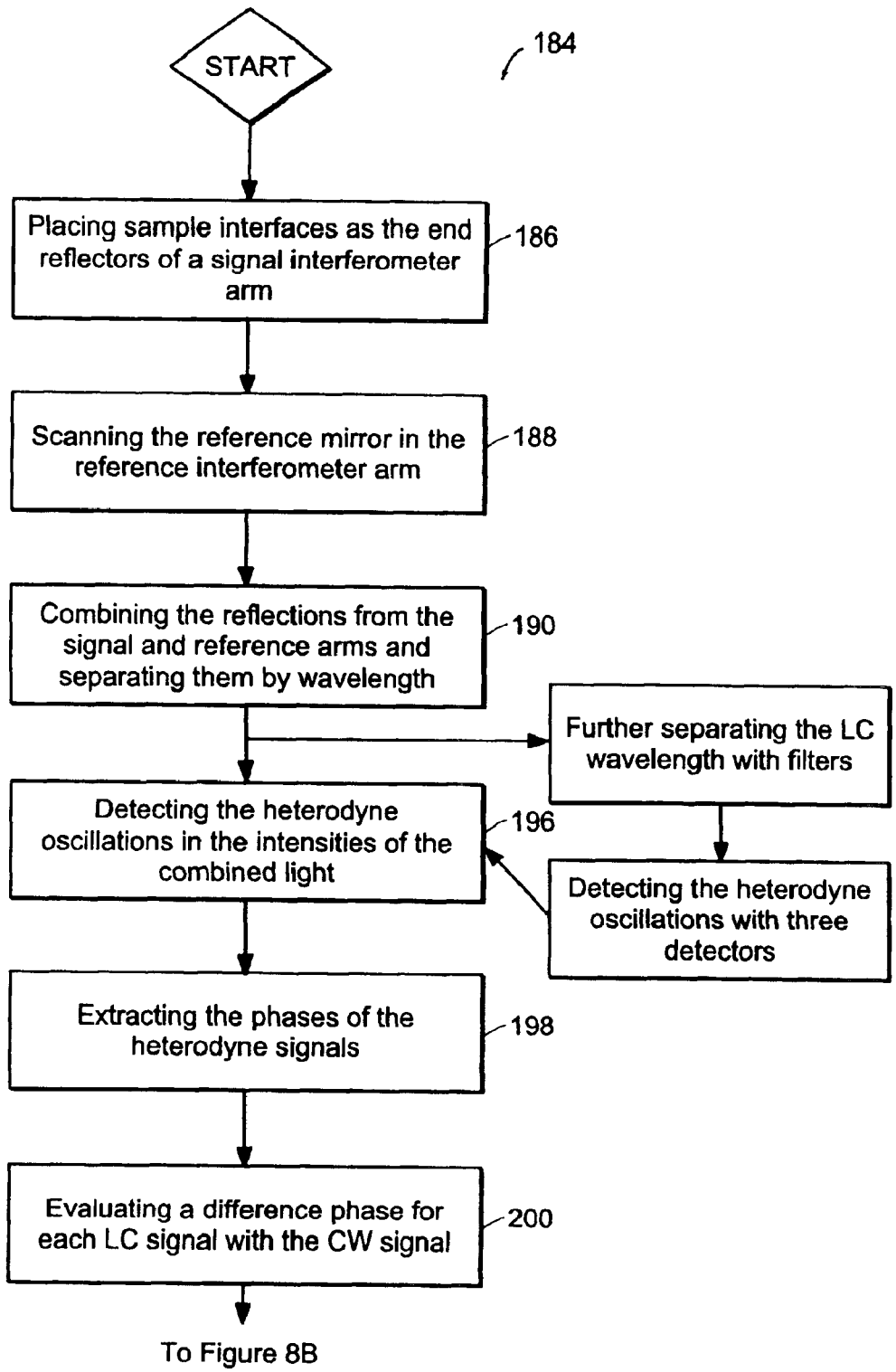
FIGS. 8A and 8B are a flow chart illustrating an alternate method to measure an optical distance in accordance with a preferred embodiment of the present invention.
Figure 8B:
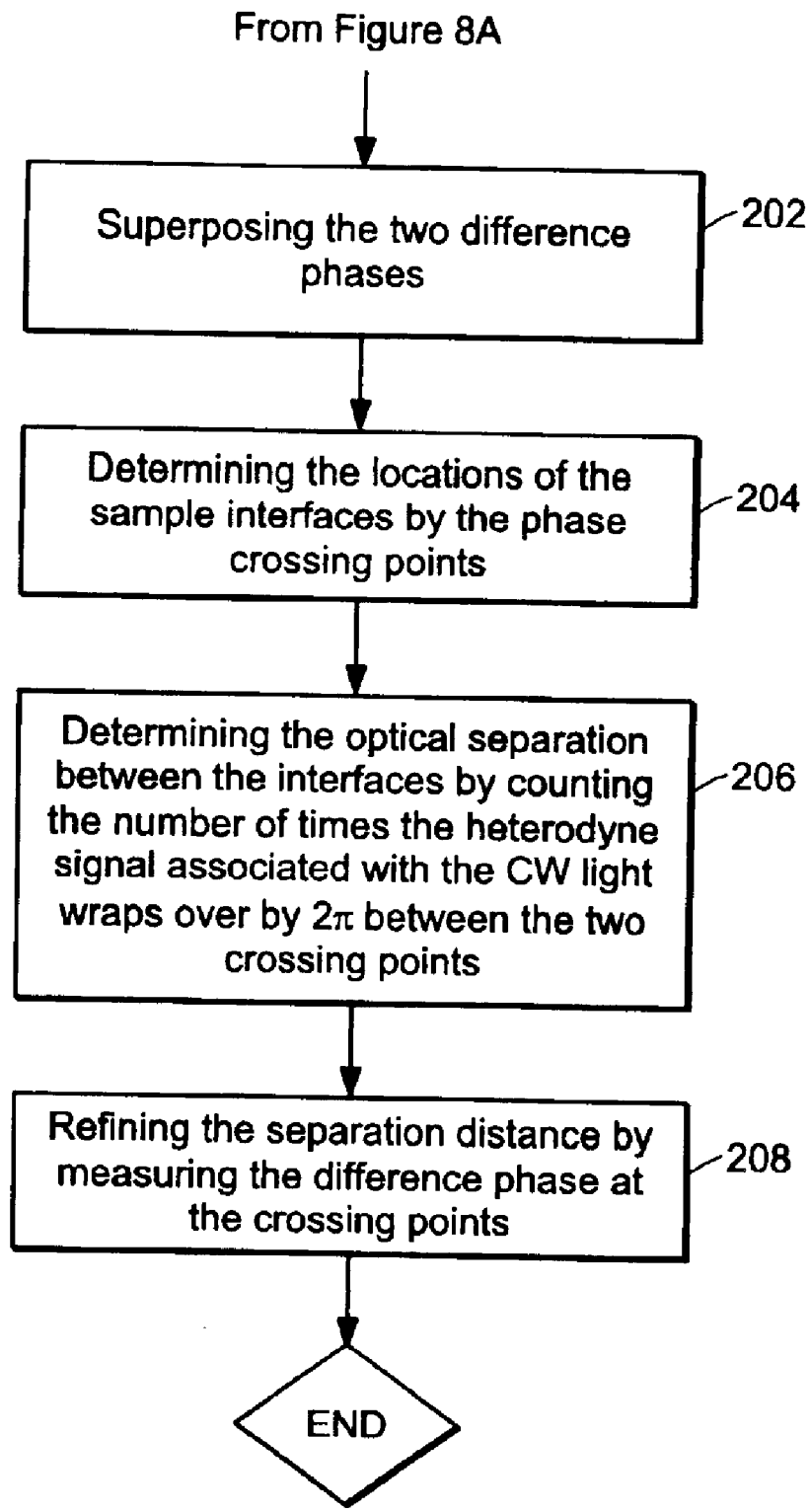

FIGS. 8A and 8B illustrate a flowchart 184 of an alternate method to measure an optical distance in accordance with a preferred embodiment of the present invention. The method 184 includes the use of two harmonically related light sources in an interferometer one of which is a CW source while the other is a low coherence source. The sample for which the optical distance needs to be measured is used as the end reflectors of the signal interferometer arm per step 186. The reference mirror in the reference interferometer arm is scanned per step 188. The method further includes the step 190 of combining the reflections from the signal and reference arms and separating them by wavelength. The low coherence wavelength is further separated using filters per step 192. The method 184 includes the step 194 of detecting the heterodyne oscillations with at least three detectors. The next step 196 includes detecting the heterodyne oscillations in the intensities of the combined light. The phases of the heterodyne signals for both wavelengths are then found via, for example, a Hilbert transform or any alternate phase extraction method per step 198. A difference phase for each low coherence signal with the CW signal is then evaluated per step 200.

The two difference phases are then superposed on each other on a graph with the x-axis representing the displacement of the reference mirror per step 202. The remaining steps 204, 206, 208 are similar to steps 140, 142, 144 as discussed with respect to FIG. 6B.

Figure 9:
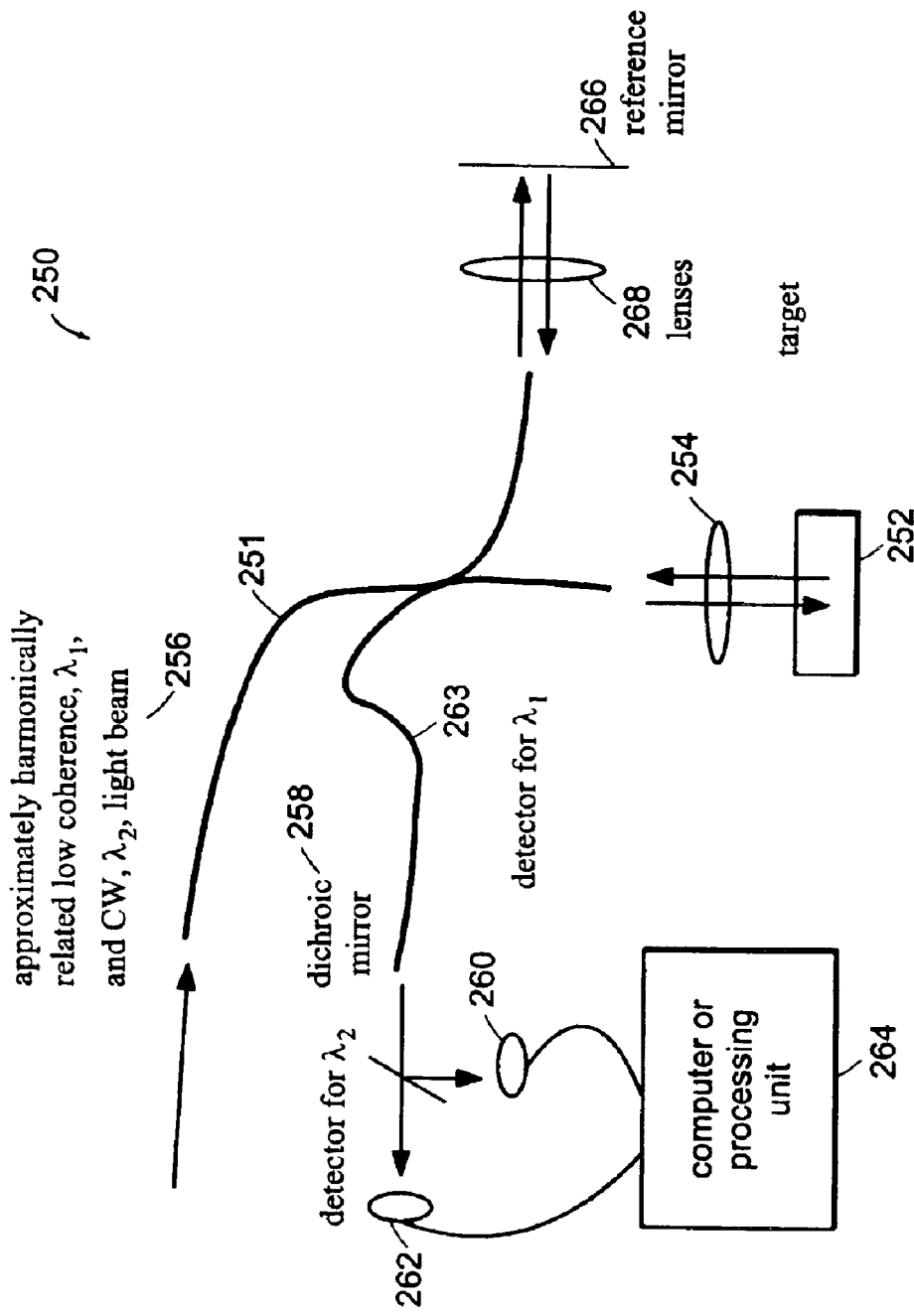
FIG. 9 schematically illustrates a preferred embodiment of a fiber based system to measure the thickness of an optically transmissive material such as a glass slab, tissue sample or layer.

The preferred embodiment of the method can be used to absolutely measure arbitrarily long optical distances with sub-nanometer precision. The preferred embodiment of the system can be free space based or fiber based. FIG. 9 illustrates a preferred embodiment of a fiber based system to measure an optical distance.

The input light 256 includes approximately harmonically related low coherence light having a wavelength $\lambda_1$ and a CW light beam having a wavelength $\lambda_2$ which travel in fiber 251. The composite beam is divided in two, one part of the signal is incident on the target lens 254 and sample 256 and travels in fiber 253 while the other is incident on the reference mirror 266 via a lens 268 and travels in fiber 251. The movement of the reference mirror introduces a Doppler shift on the reflected beam. The reflected beams are recombined and then separated into their component wavelength components by means of the dichroic mirror 258. These wavelength components are measured separately with photodetectors 260, 262. The resulting heterodyne signals at their respective Doppler-shifted frequencies are bandpassed around their respective center heterodyne frequencies and Hilbert transformed to extract the corresponding phases of the heterodyne signals, $\psi_{CW}$ and $\psi_{LC}$.

The preferred embodiment methods can be used to make precise optical distance measurements. From such measurements, optical properties of target objects can be accurately measured. By measuring the dispersion profile of the target, structural and/or chemical properties of the target can be evaluated. In the biomedical context, preferred embodiments of the present invention can be used to accurately determine the dispersion property of biological tissues in a non-contact and non-invasive manner. Such dispersion determination can be used on the cornea or aqueous humor of the eye. The sensitivity achieved can be sufficient to detect glucose concentration dependent optical changes. In a preferred embodiment of the present invention method, the blood glucose level can be determined through non-invasive measurements of the dispersion profile of either the aqueous, vitreous humor or the cornea of the eye.

As discussed hereinbefore, phase based interferometry methods are able to measure optical distances very sensitively. However, they are typically limited in their applications by a problem that is widely known in the field as the $2\pi$ ambiguity problem. The crux of this problem is that it is impossible to differentiate a length of 10.1 wavelengths from the length of 11.1 wavelengths. The preferred embodiments of the present invention overcome this limitation and allow absolute optical distance measurements with sub-nanometer accuracy.

There are numerous phase based methods that measure changes in optical distances with a sensitivity of approximately the nm range. As long as the change is small and gradual, the change can be continuously tracked. There are low coherence methods that measure absolute optical distance by tracking the delay in arrival at the detector of light reflected from different interfaces of the reflector sensitivity in approximately microns. As discussed hereinbefore, the simultaneous use of a CW and a low coherence light sources in an interferometer provides for the methods to measure optical distance. The heterodyne phases of the signals associated with the two wavelengths are intrinsically related. By processing the phase per the preferred embodiments, motional noise is minimized and preferably eliminated from our measurements.

An application of a preferred embodiment is the glucose level determination using the measurement of the refractive index of the vitreous and/or aqueous humor of the eye. The sensitivity of this technique affords the ability to measure chemical concentrations with a sensitivity that is clinically relevant. One of the more obvious applications of the method of a preferred embodiment is the determination of blood glucose level through measurements performed on the eye. The glucose level of the fluid in the eye mirrors that of the blood with clinical insignificant time delay.

Figure 10:
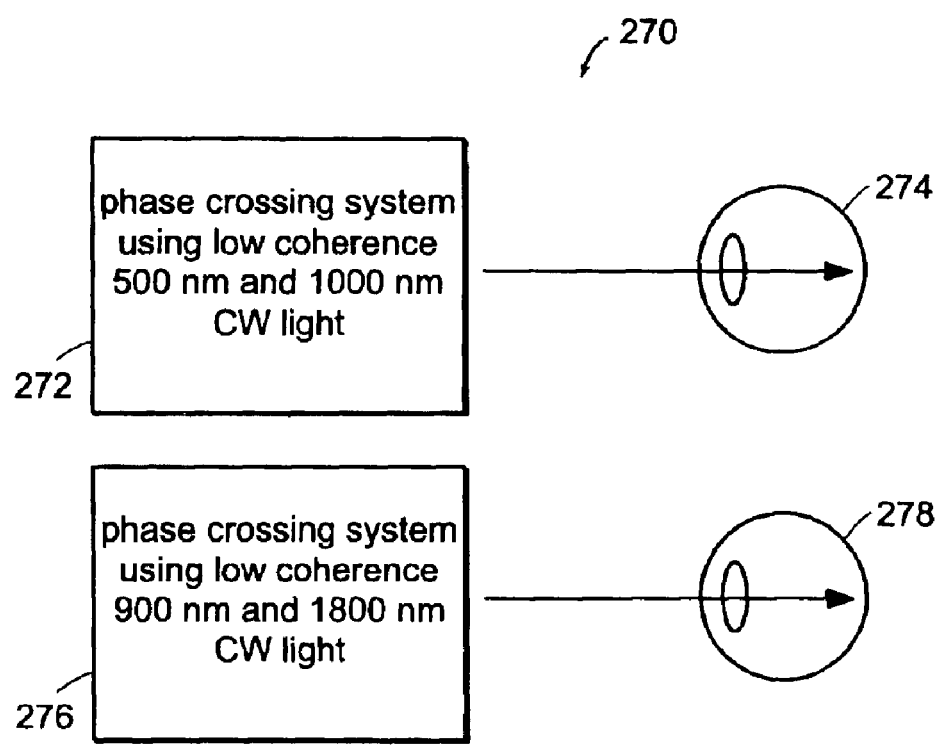
FIG. 10 illustrates a preferred embodiment of the present invention system used in a vitreous and/or aqueous humor glucose measurement system in accordance with the present invention.

The method of a preferred embodiment measures the optical path lengths of the vitreous and/or aqueous humor layer in the eye at least two separate sets of wavelengths as illustrated in FIG. 10. The method measures the product of the refractive index at the low coherence wavelength and the physical separation between two interfaces. By changing the wavelength of the low coherence light source (and appropriately changing the CW wavelength to match), the refractive index difference at different wavelengths is measured. For example, one set of experiment is performed with a tunable 500 nm low coherence light source and a one micron CW light source to extract $n_{500nm}L$ where L is the physical thickness of the vitreous and/or aqueous humor at the point of measurement. Another set of experiments is performed with a tunable 1000 nm low coherence light source and a 1800 nm CW light source to extract $n_{900nm}L$. By taking the ratio of these two measurements, the refractive index ratio, $n_{500nm}/n_{900nm}$, of the vitreous and/or aqueous humor is extracted. With the existing sensitivity, for example, 0.5 nm optical path sensitivity, a preferred embodiment of the system, the ratio $n_{500nm}/n_{900nm}$ with $10^{-8}$ sensitivity can be measured for a material of thickness equal to that of the human vitreous and/or aqueous humor. This provides the sensitivity to changes in the glucose level of about 0.25 mg/dl. Given that the typical blood glucose level is about 100 mg/dl, a preferred embodiment of the present invention is well suited for blood glucose assessment. The choice of optical wavelengths is flexible, the wavelength used hereinabove is simply for illustration purpose. For maximal sensitivity, the wavelength separation is preferably as large as possible. Preferred embodiments include a separation of greater than 500 nm.

In the event that such a refractive index ratio is insufficient for absolute blood glucose level determination due to the presence of other chemicals that is changing in the vitreous and/or aqueous humor, a more complete range of optical path length measurement can be made at a range of other wavelengths. This set of more complete measurement allows the determination of glucose level and other chemical concentrations by fitting the measurements to known dispersion profiles of glucose and other chemicals.

A preferred embodiment of the present invention can be applied as a measurement technique in semiconductor fabrication. As the preferred embodiment of the method is non-contact and non-destructive, it can be used to monitor the thickness of semiconductor structures as they are being fabricated. In addition, the composition of the semiconductor structures can be assessed in much the same manner as that discussed with respect to the characterization of the vitreous and/or aqueous humor measurements.

The claims should not be read as limited to the described order or elements unless stated to that effect. Therefore, all embodiments that come within the scope and spirit of the following claims and equivalents thereto are claimed as the invention.

What is claimed:

1. A method of measuring an optical distance comprising the steps of:
   providing a first wavelength of coherence light and a second wavelength of light;
   directing light of the first wavelength and the second wavelength along both a first optical path and a second optical path, the first optical path extending onto a medium to be measured and the second path undergoing a change in path length;
   detecting light from the medium and light from the second optical path to measure a first change in phase of light interacting with the medium;
   adjusting the first wavelength of light to generate a third wavelength of low coherence light;
   directing light of the third wavelength and the second wavelength along both the first optical path and the second optical path, the first optical path extending onto the medium to be measured and the second path undergoing a change in path length;
   detecting light from the medium and light from the second optical path to measure a second change in phase of light interacting with the medium;
   superposing the first change in phase and the second change in phase to determine at least two phase crossing points; and
   determining the optical distance by counting the number of continuous interference fringes between the at least two phase crossing points.

2. The method of claim 1 wherein the medium comprises biological tissue.

3. The method of claim 1 wherein the medium comprises a semiconductor material.

4. The method of claim 1 further comprising the step of refining the optical by measuring the difference phase at the at least two phase crossing points.

5. The method of claim 1 wherein the step of changing the first wavelength of light comprises adjusting a center wavelength by approximately 2 nm.

6. The method of claim 1 further comprising providing a light source that emits the first wavelength and a second wavelength that are harmonically related.

7. The method of claim 1 further comprising providing a first low coherence light source and a second continuous wave light source.

8. A method for measuring an optical distance, comprising the steps of;
   providing a first signal and a second signal generated by a first low coherence light source and a third signal generated by a second light source, the first light source being harmonically related to the second light source;
   determining a first heterodyne signal from the first and the third signal and a second heterodyne signal from the second and third signal; and
   determining the phase relationship between the first and second heterodyne signals to obtain the optical distance.

9. The method of claim 8 wherein the first signal and second signal are low coherence signals having a difference in wavelength of at least 1 nm.

10. The method of claim 8 wherein the third signal is a continuous wave signal.

11. The method of claim 8 wherein providing the first and the second signals are generated by a broadband light source.

12. A system for measuring an optical distance, comprising the steps of:
   a first low coherence light source that generates a first signal and a second signal;
   a second light source that generates a third signal, the first low coherence light source generating signals that are harmonically related to the third signal from the second light source;
   a detector system that measures a first heterodyne signal from the first and the third signal and a second heterodyne signal from the second and third signal; and
   a processor that determines a phase relationship between the first and second heterodyne signals to obtain the optical distance.

13. The system of claim 12 wherein the first signal and second signal are low coherence signals.

14. The system of claim 12 wherein the third signal is a continuous wave signal.

15. The system of claim 12 wherein the first and the second signals are generated by a broadband light source.

16. The system of claim 12 further comprising an optical pathway including an optical fiber.

17. The system of claim 12 further comprising a low coherence signal having a bandwidth of at least 5 nm.

18. The system of claim 12 wherein the system comprises an interferometer.

19. The system of claim 12 further comprising a mirror and a scanner that scans the mirror from a first position to a second position.

20. The system of claim 12 wherein the detector system comprises a first detector that detects a first signal and a second detector that detects a second signal harmonically related to the first signal.

21. The system of claim 12 further comprising an analog to digital converter in communication with the processor.

22. The system of claim 12 wherein the first light source is a laser Source.

23. The system of claim 16 wherein the continuous wave signal is generated by a semiconductor laser.

24. The system of claim 12 wherein the system measures optical distance.

25. The system of claim 12 wherein the system measures refractive index of the medium.

26. The system of claim 12 wherein the medium comprises biological tissue.

27. The system of claim 12 wherein the detector further comprises a filter.

28. The system of claim 12 wherein the system counts a number of interference fringes between phase crossing points.

29. The system of claim 12 wherein the system measures a thickness of the medium.

30. A method of measuring a characteristic of biological tissue, comprising the steps of:

providing a first signal and a second signal generated by a first low coherence light: source and a third signal generated by a second light source, the first light source generating a signal that is harmonically related to a signal from the second light source;

determining a first heterodyne signal from the first and the third signal and a second heterodyne signal from the second and third signal; and determining a phase relationship between the first and second heterodyne signals to obtain the characteristic of biological tissue.

31. The method of claim 30 further comprising determining a dispersion profile of the biological tissue.

32. The method of claim 30 wherein the first signal and second signal are low coherence signals having a difference in wavelength of at least 1 nm.

33. The method of claim 30 wherein the third signal is a continuous wave signal.

34. The method of claim 30 wherein the step of providing the first and the second signals includes using a broadband light source.

35. The method of claim 30 wherein the biological tissue comprises at least one of the cornea, the aqueous humor and vitreous humor.

36. The method of claim 30 further comprising detecting a blood glucose level using a dispersion profile.

37. The method of claim 30 further comprising determining refractive index variations at a plurality of wavelengths using a dispersion profile.

38. The method of claim 30 further comprising determining a refractive index of the biological tissue.

* * * * *

UNITED STATES PATENT AND TRADEMARK OFFICE
CERTIFICATE OF CORRECTION

| | | |
|---|---|---|
| PATENT NO. | : 6,934,035 B2 | Page 1 of 1 |
| APPLICATION NO. | : 10/024455 | |
| DATED | : August 23, 2005 | |
| INVENTOR(S) | : Changhuei Yang et al. | |

It is certified that error appears in the above-identified patent and that said Letters Patent is hereby corrected as shown below:

Column 1, following "GOVERNMENT SUPPORT" please delete lines 6-8 and insert the new paragraph as follows:

--This invention was made with government support under Grant No. P41 RR002594, awarded by the National Institutes of Health. The government has certain rights in this invention.--

Signed and Sealed this

Seventeenth Day of May, 2011

David J. Kappos
*Director of the United States Patent and Trademark Office*